(12) United States Patent
van Amerongen et al.

(10) Patent No.: US 6,231,915 B1
(45) Date of Patent: *May 15, 2001

(54) STANOL COMPRISING COMPOSITIONS

(75) Inventors: Marnix P. van Amerongen, Vlaardingen (NL); Lourus Cornelis Lievense, Valinhos (BR)

(73) Assignee: Lipton, division of Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/135,721

(22) Filed: Aug. 18, 1998

(30) Foreign Application Priority Data

Aug. 22, 1997 (EP) .................................................. 97202598

(51) Int. Cl.$^7$ ................................ A23D 7/005; C07J 9/00
(52) U.S. Cl. .......................... 426/611; 426/602; 426/603; 552/544; 552/545
(58) Field of Search .................................. 426/601, 602, 426/603, 611; 552/544, 545; 514/182

(56) References Cited

U.S. PATENT DOCUMENTS

| | | | |
|---|---|---|---|
| 3,617,308 | 11/1971 | Graffelman . | |
| 3,956,522 | 5/1976 | Kattenberg et al. . | |
| 4,044,168 | 8/1977 | Steenhoek et al. . | |
| 5,244,887 | * 9/1993 | Straub | 514/182 |
| 5,502,045 | * 3/1996 | Miettinen | 514/182 |
| 5,892,068 | * 4/1999 | Higgins | 552/554 |
| 5,958,913 | * 9/1999 | Miettenen | 514/182 |
| 6,025,348 | * 2/2000 | Goto | 514/182 |
| 6,031,118 | * 2/2000 | van Amerongen | 552/544 |

FOREIGN PATENT DOCUMENTS

| | | |
|---|---|---|
| 041 303 | 12/1983 | (EP) . |
| 0 209 176 | 1/1987 | (EP) . |
| 0 249 282 | 12/1987 | (EP) . |
| 0 470 658 | 12/1992 | (EP) . |
| 594 612 | 8/1997 | (EP) . |
| WO92/19640 | * 11/1992 | (FI) . |
| 1 405 346 | 9/1975 | (GB) . |
| 143 115 | 6/1967 | (NL) . |
| 178 559 | 8/1974 | (NL) . |
| 155177 | 9/1975 | (NL) . |
| 155 436 | 5/1976 | (NL) . |
| 149 687 | 8/1977 | (NL) . |
| 92/19640 | 12/1992 | (WO) . |
| 98/01126 | 1/1998 | (WO) . |
| 98/06405 | 2/1998 | (WO) . |
| 98/19556 | 5/1998 | (WO) . |

OTHER PUBLICATIONS

Euopean Search Report 98 202588.
Japanese Abstract 62 055040, published Oct. 3, 1987.

* cited by examiner

*Primary Examiner*—Carolyn Paden
(74) *Attorney, Agent, or Firm*—Gerard J. McGowan, Jr.

(57) ABSTRACT

The invention regards a process for the preparation of a mixture of stanol and stanol fatty acid esters by esterification of phytosterols with a source for fatty acid moieties, in such a way that the degree of esterification of the phytosterols is in the range of 40–85%, and subsequent hardening of the so obtained sterol/sterol fatty acid mixture, the process can be carried out without the use of any solvent, and wherein preferably the fatty acid groups of the stanol fatty acid esters are substantially saturated fatty acid esters. Also claimed are food products comprising mixtures of stanol and stanol fatty acid esters, in particular fat based food products such as yellow fat spreads.

15 Claims, No Drawings

STANOL COMPRISING COMPOSITIONS

BACKGROUND OF THE INVENTION

The present invention concerns a method for the production of stanol fatty acid esters, a stanol fatty acid ester composition, and the use thereof in food products, in particular in fat based food products in amounts sufficient to obtain a blood cholesterol lowering effect if the food product is used according to the common needs of the consumer.

Fatty acid esters of phytosterols and/or phytostanols are hydrolysed in the gut and the subsequent free phytosterols and/or phytostanols will inhibit the absorption of cholesterol thereby lowering the blood cholesterol. Free phytosterols and/or phytostanols themselves are hardly absorbed. Indications in literature are that phytostanols are absorbed even in a lesser extend than phytosterols. The use of phytostanols in fat based food products to lower blood cholesterol could therefore be preferred over the use of phytosterols.

In U.S. Pat. No. 5,502,045 (Raision Tehtaat Oy AB) a substance of beta-sitostanol fatty acid ester is described produced by 1. solvent hardening of beta-sitosterol followed by 2. esterification of the formed beta-sitostanol with fatty acids. The so formed mixture of beta-sitostanol fatty acid esters can be used as such or added to a food.

There are several disadvantages to this production method, of which the most severe is that the beta-sitosterol should first be solubilized in a solvent (e.g. ethylacetate, butanol, ethanol) before the hardening of the sterol can be performed. Because the solubility of beta-sitosterol, or phytosterols in general, in solvents is rather limited, the hardening step is a relatively expensive operation because of high solvent costs and high costs of hardening equipment of relatively large volume. Moreover, the solvents need to be recovered after the hardening process is completed, and suitable locations for above hardening process will be limited because of environmental regulations. Furthermore, in a process aiming at the production of a food ingredient, removal of all solvents is essential, this making the process even more expensive.

It has been observed that the stability of fat based food products diminishes by the addition of sterols and stanols thereto, in particular when the sterols/stanols are used at higher levels. As sterols and stanols are not very soluble in fat large crystals thereof are found in the products prepared with these sterols or stanols. For example, very serious crystal formation is observed at 3–4% sterol levels On the other hand, however, the use of these higher levels is often required to obtain the significant cholesterol reduction level that is desired.

It is well known that by esterification of sterols/stanols with fatty acids, the solubility can be increased. However, a disadvantage of esterification is that this decreases the efficacy of the sterol/stanol compounds to lower the blood cholesterol level. Another disadvantage found in the use of sterol/stanol fatty acid esters is that the absorption of lipophilic micronutrients (like beta-carotene) decreases (Gyling HK et al (1996) Circulation 6: I-578).

Another disadvantage found with the esterification of sterols/stanols is found in the production thereof, requiring long processing times and/or high processing costs.

SUMMARY OF THE INVENTION

The disadvantages indicated above were found to be reduced with the present invention, which concerns a process for the production of a stanol and stanol fatty acid ester mixture, by esterification of phytosterols with a source for fatty acid moieties in such a way that the degree of esterification of the sterols is in the range of 40%–85%, and subsequent hardening of the so obtained sterol/sterol fatty acid ester mixture. Preferably, the degree of esterification is in the range of 50–85%, more preferably in the range of 55–80%, and most preferably in the range of 60–70%. This process allows a preparation of mixtures of stanols and stanol fatty acid esters without the presence of a solvent needed in any of the process steps. Sources for fatty acid moieties, are the known compounds, normally applied in esterification reactions. Preferred sources are free fatty acids and triglycerides.

This invention allows that a significant cost reduction can be achieved, as the amount of the relatively expensive sterols used as the starting material can be reduced without a decrease of comparable blood cholesterol lowering efficacy of the end product, whereas a further reduction of costs is obtained in the time and processing reduction of the esterification process of the sterols. By partial esterification of the sterols and subsequent hardening of the sterol/sterol ester mixture so obtained no solvents in the hardening step are needed since the sterolester mixture is in a liquid state. Using such a solvent free production method, which is more environmental friendly, and does not require specific legal admissions, is also more cost effective due to the fact that less raw materials, equipment and labour is required.

Hence, advantages are found in minimization of possible negative side effects and optimization of efficacy, quality (solubility) and production costs.

Where in this application sterols are mentioned, phytosterols (4-desmethylsterols, 4-monomethylsterols and 4,4'-dimethylsterols, and/or mixtures thereof) are meant. When stanols are mentioned the stanol analogous of above molecules and mixtures thereof are meant.

For obtaining the sterolester mixture before hardening is carried out, the sterols are esterified with a source for one or more C2–24 fatty acids moieties to an esterification degree in the range of 40–85%, more preferably in the range of 50–80% and most preferably in the range of 60–70%. For the purpose of the invention the source for fatty acid moieties can be indicated with the term C2–24 fatty acid and this refers to any molecule comprising a C2–24 main chain and at least one acid group. Although not preferred within the present context the C2–24 main chain may be partially substituted or side chains may be present. Preferably, however the C2–24 fatty acids are linear molecules comprising one or two acid group(s) as endgroup(s). Most preferred are linear C8–22 fatty acids as occur in natural oils. Suitable esterification conditions are for example described in WO 92/19640.

Suitable examples of any such fatty acids are acetic acid, propionic acid, butyric acid, caproic acid, caprylic acid, capric acid. Other suitable acids are for example citric acid, lactic acid, oxalic acid and maleic acid. Preferred are lauric acid, palmitic acid, stearic acid, arachidic acid, behenic acid, oleic acid, cetoleic acid, erucic acid, elaidic acid, linoleic acid and linolenic acid.

Most preferred are the C18 polyunsaturated, monounsaturated or saturated fatty acids like stearic acid, oleic acid, elaidic, linoleic acid, alpha-linolenic acid and gamma-linolenic acid, since after fully hardening of sterolesters comprising these fatty acids, the fatty acid part will be the saturated stearic acid, which has a neutral effect on blood cholesterol.

When desired a mixture of fatty acids may be used. It is also possible to use a natural occurring fat or oil as a source of the fatty acid moieties and to carry out the esterification via an interesterification reaction herewith. Most preferred are fatty acid mixtures containing high amounts (>70%) of C18 polyunsaturated, monounsaturated or saturated fatty acids such as fatty acid mixtures of sunflower, safflower, rapeseed, linseed, linola and/or soybean.

The invention further concerns the stanol and stanol fatty acid ester mixture so produced. Also claimed are stanol and stanol fatty acid esters mixtures wherein the fatty acid groups of the stanol fatty acid esters are substantially saturated fatty acid groups, and preferably, >85% are saturated, more preferably >90%, and most preferably >95% are saturated.

The invention further describes food products comprising such a mixture. The food products of the invention comprise at least 1% of stanol equivalents (present as free stanols and stanol fatty acid esters) whereby the degree of esterification is in the range of 40–85%. It has been observed that such products do not show instability and/or crystal formation, whereas the maximum blood cholesterol lowering efficacy of the stanols is obtained, while negative effects on absorption of lipophilic micro-nutrients are avoided. This beneficial effect is in particular suitable for products comprising at least 5% of a mixture comprising 15–50% stanols and 50–85% stanol fatty acid esters.

The invention was found to be in particular beneficial at stanol levels above 3 wt. % (total of stanol and stanol ester mixture), and more preferably at levels of at least 5 wt. %. Normally, a total stanol (equivalents) level range of 7–15 wt % provides sufficient to good results when applied in daily consumed food products.

As mentioned, it has been found that the majority of the stanols does not have to be esterified to produce a decent and effective blood cholesterol lowering fat based food product. Moreover, it has been found that esterification of all or nearly all of the stanols decreases the efficacy of these compounds to lower blood cholesterol. Furthermore it is anticipated that the decrease of absorption of lipophilic micronutrients (like beta-carotene) will be less than earlier reported (Gyling HK et al (1996) Circulation 6: I-578) when less of the sterols in the food product are esterified.

DETAILED DESCRIPTION OF THE INVENTION

A specific embodiment of this invention regards the use of a stanol and stanol fatty acid mixture in fat based food products. Fat based food products are food products (partially) based on fat and regarded by the consumer, as 'fatty type of products'. Examples are yellow fat spreads (containing vegetable fat and/or animal fat such as butterfat), dressings, coffee-creamer, shortenings, cooking and frying oils, fillings and toppings, ice-cream and the like. These products in most cases comprise a particular amount of fat. In some cases, however, products are still regarded as 'fatty type of products', despite a replacement of part or even all of the fat by fat replacers. Fat based food products in which the fat is partially or completely replaced by fat replacers are also covered by the term fat based food products of this invention.

The food products as such are common products in the western world, and are used by consumers on a daily basis in amounts different for each individual. The invention is in particular very suitable for yellow fat spreads, dressings, cheese, shortenings, cooking and frying oils and ice cream, with a preference for yellow fat spreads, mayonnaise, dressings, shortenings, cooking and frying oils. On the basis of habits of the consumer in the western world, the invention is preferred to concern in particular for yellow fat spreads (including margarines, butter and low fat spreads) and dressings. Yellow fat spreads, for this invention, can comprise 0 (zero) to 90% fat (usually 5–80%). Dressings can comprise 0 to 85% fat (usually 5–80%), shortenings, cooking and frying oil more than 95% fat.

The most advantageous level of sterols to be esterified within the teaching of the present invention depends on the fat level in the food product and the total level of stanols (including the stanol fatty acid esters) therein. At a given total stanol amount in the product, the most advantageous degree of esterification will be lower for high fat levels than for low fat levels (based on total food product). For example, at total stanol equivalent levels of about 10% and at fat levels in the range of 50–90%, the degree of esterification is suitably optimized in the range of 40–75%, whereas at a total stanol equivalent level of about 10% and a fat level in the range of 0–50%, the degree of esterification optimum will be found in the range of 60–90%.

Also, higher stanol equivalent levels at given fat level will lead to optimization at higher degrees of esterification.

The preparation of the fat based food products comprising the stanol fatty acid esters of the invention can be carried out in any suitable manner commonly known. Suitably, the stanol fatty acid ester mixture can be added and dissolved to the fat prior to combining with the aqueous phase of the product to be prepared.

In a preferred embodiment, the food product is a yellow fat spread comprising 0 to 80% fat, and at least 1 wt. % and preferably at least 2 wt. % and more preferably at least 5 wt % stanol equivalents (present as free stanols and stanol ester mixture prepared according to the invention). In its most preferred embodiment, the amount of stanol equivalents is at least 5%, with optimal results found when the amount of stanol equivalents is in the range of 7–15%.

The invention is in particular suitable for low fat spreads having a fat level in the range of 0–40%, where the amount of cholesterol level reducing fat is low. However, another preference exists for higher fat level spreads (60–80% fat), as a very significant reduction of cholesterol level in the blood serum can be obtained when high PUFA fat level fats are used, and where the fat in the spread is not optimised on PUFA, to add the cholesterol lowering effect upon use to such spreads.

The fat that is applied in these fat based food products can be any fat, such as dairy fat and/or vegetable fat. However, if fat is present, for health reasons the use of one or more vegetable fat sources is preferred. In particular, the use of liquid fats is preferred.

The fat can be one single fat or a blend. The use of fat compositions comprising a considerable amount of PUFA rich triglycerides in addition to the use of the stanol/stanol fatty acid ester mixture is in particular considered highly beneficial. For example, oils of sunflower, safflower, rapeseed, linseed, linola and/or soybean can be used in a preferred embodiment. Also the fat compositions mentioned in Netherlands patent documents no. NL 143115, NL 178559, NL 155436, NL 149687, NL 155177, European patent documents EP 41303, EP 209176, EP 249282, and EP 470658 are highly suitable.

If a fat blend is used, it is preferred that it comprises at least 30%, and more preferred at least 45% of polyunsaturated fatty acids, based on the total weight amount of the fat in the fat based food product. So, a strong effect on the cholesterol lowering effect is obtained if use is made of an optimal ratio of stanol and stanol-esters as set forth in this application in a food product in which a fat blend comprising at least 30 wt. % of PUFA rich triglycerides is used.

As fat spreads are a commonly and daily used product in western food eating habits, a preference exists for the use of a mixture of stanol and stanol fatty acid esters, in all the preferred embodiments as set forth above, in fat spreads.

Where butterfat is used for preparing spreads of the invention, or where the spreads are butter, it is preferred that the amount of stanol equivalents is in the range of 5–15%, preferably 10–15%. As the consumption of butter is considered less beneficial for consumers health, the present invention is in particular suitable for making spreads containing butter or butter-melanges, as the negative effect associated with the butter consumption can be minimized or even reversed.

Another advantage of the present invention is that stanol ester produced by esterification to a degree of 40–85% and subsequent hardening (i.e. stanol esters with saturated fatty acids) have a stronger structuring properties than stanolesters mixtures comprising mainly mono- or poly-unsaturated fatty acids, due to their higher melting points. By using the so produced stanol and stanol esters with saturated fatty acids, the amount of hardstock required to make a spreadable product out of above mentioned liquid oils can be more reduced than with stanolesters mixtures comprising mainly mono- or poly-unsaturated fatty acids, thereby potentially optimizing the amount of PUFA rich glycerides in the product further, and thereby compensating the saturated fatty acid part of the stanol ester mixture applied in the product.

EXAMPLES

Example 0a

Partial Esterification of Sterols to Sterolesters with an Optimal Esterification Degree by Stopping Reaction A mixture of sterols derived from soybean oil distillates was partially esterified with sunflowerseed oil fatty acid methylesters in such a way that an optimal ratio between free sterols and sterolesters was obtained.

A mixture of 60.8 kg sterols and 43.8 kg sunflowerseed oil methylesters was dried for 2 hours at 120 degree C. under a reduced pressure of 5–40 mbar. Then the interesterification was started by adding 120 g of sodium methylate catalyst under a reduced pressure of 30–40 mbar and at 125 degree C. After 1 h and 15–30 minutes the mixture was cooled to 90 degree C. and the reaction was stopped by adding 10% of a diluted citric acid aqueous solution. An esterification or conversion degree of about 60% was obtained. After washing, the water was separated and the mixture was dried and bleached. The residual methylesters were removed by stripping/deodorisation.

Example 0b

Esterification of Sterols to Sterolesters with a Maximal Esterification Degree and Optimizing the Free Sterol to Sterolester Ratio Afterwards Firstly, a mixture of sterols derived from soybean oil distillates was fully esterified with sunflowerseed oil fatty acid methylesters.

A mixture of 60.8 kg sterols and 43.8 kg sunflowerseed oil methylesters was dried for 2 hours at 120 degree C. under a reduced pressure of 5–40 mbar. Then the interesterification was started by adding 120 g of sodium methylate catalyst under a reduced pressure of 15–30 mbar and at 125 degree C. After 2 h and 30 minutes the mixture was cooled to 90 degree C. and the reaction was stopped by adding 10% of a diluted citric acid aqueous solution. An esterification or conversion degree of about 91% was obtained. After washing, the water was separated and the mixture was dried.

Secondly, 23.4 kg of unesterified sterols were added and dissolved to obtain an optimal esterification degree of about 60%. Next this mixture was bleached and the residual methylesters were removed by stripping/deodorisation.

Example 1a

Hydrogenation of Free Sterol and Steryl Esters from Ex.0a

A mixture of free sterols and sterols esters as obtained from Example 0a was hydrogenated on laboratory scale. As catalyst 5 wt % Pd on activated carbon was used. To 0.5 kg of the sterylesters 2 g of catalyst was added and the mixture was heated to 90 degree C. under a reduced pressure of 5–30 mbar.

The hydrogenation was carried out at 90 degree C. and at 3 bar hydrogen pressure. After 90 minutes approximately 40% of the theoretical amount of hydrogen was absorbed and again 2 g of catalyst was added. After 7.5 hours approx. 80% of the theoretical amount of hydrogen was absorbed and 2 g of catalyst was added and the temperature was increased to 95–115 degree C. Finally, after 11 hours of reaction approx. 100% of the theoretical amount of hydrogen was absorbed. At that moment no extra hydrogen was absorbed anymore and the hydrogenation was ended.

The major part of the catalyst was removed by filtration over a paper filter. The remaining part of the catalyst was removed by applying 2% Hyflow and filtration over a paper filter.

Analysis indicated that a hardening conversion of about 95% was achieved.

Example 1b

Hydrogenation of Free Sterol and Steryl Esters from Ex.0b

A mixture of free sterols and sterols esters as obtained from Example 0b was hydrogenated on laboratory scale. As catalyst 5 wt % Pd on activated carbon was used. To 0.5 kg of the sterylesters 2 g of catalyst was added and the mixture was heated to 90 degree C. under a reduced pressure of 5–30 mbar.

The hydrogenation was carried out at 90 degree C. and at 3 bar hydrogen pressure. After 90 minutes approximately 40% of the theoretical amount of hydrogen was absorbed and again 2 g of catalyst was added. After 7.5 hours approx. 80% of the theoretical amount of hydrogen was absorbed and 2 g of catalyst was added and the temperature was increased to 95–115 degree C. Finally, after 11 hours of reaction approx. 100% of the theoretical amount of hydrogen was absorbed. At that moment no extra hydrogen was absorbed anymore and the hydrogenation was ended.

The major part of the catalyst was removed by filtration over a paper filter. The remaining part of the catalyst was removed by applying 2% Hyflow and filtration over a paper filter.

Analysis indicated that a hardening conversion of about 95% was achieved.

Example 2a

Preparation of a Spread 70% Fat (Stanol esters Ex.1a)

Refined sunflower oil (65% PUFA as linoleic acid) was enriched with esterified stanols as obtained from Example 1a (to a total stanol equivalent concentration of 45%). Of this stanol-ester concentrate, 22 parts were mixed with 35 parts of normal refined sunflower oil, 15 parts of refined rapeseed oil and 8 parts of a refined interesterified mixture of 65 parts fully hardened palm oil and 35 parts fully hardened palm kernel oil. To this fatblend, small amounts of soybean lecithin, monoglyceride, flavours and beta-carotene solution were added.

To 18 parts water, small amounts of whey protein powder, flavour, and citric acid were added to obtain a pH of 4.8.

80 parts of the fat phase composition (containing 70% of fat) and 20 parts of the aqueous phase composition were mixed and kept at 60 degree C. The mixture was then passed through a Votator line with 2 scraped surface heat exchangers (A-units) and 1 stirred crystallizer (C-unit) in AAC-sequence operating at 800, 800 and 100 rpm respectively. The product leaving the C-unit had a temperature of 11 degree C. It was filled into tubs and stored at 5 degree C. A good and stable, high PUFA, high fat-continuous spread enriched with 10% stanol equivalents (mainly present as C18:0 stanol esters) was obtained.

Example 3a

Preparation of a Spread 40% (Stanol Esters Ex.1a)

Refined sunflower oil (65% PUFA as linoleic acid) was enriched with esterified stanols as obtained from Example 1a (to a total stanol equivalent concentration of 45%). Of this stanol-ester concentrate, 22 parts were mixed with 23 parts of normal refined sunflower oil and with 5 parts of a refined interesterified mixture of 50 parts fully hardened palm oil and 50 parts fully hardened palm kernel oil. To this fatblend small amounts of soybean lecithin, monoglyceride and beta-carotene solution were added.

To 44 parts water, gelatine and small amounts of whey protein powder, flavours, preservative and citric acid were added to obtain a pH of 4.7.

50 parts of the fat phase composition (containing 40% of fat) and 48 parts of the aqueous phase composition were mixed and kept at 60 degree C. The mixture was then passed through a Votator line with 2 scraped surface heat exchangers (A-units) and 2 stirred crystallizers (C-unit), in ACAC-sequence operating at 500, 1000, 600 and 100 rpm respectively. The product leaving the last C-unit had a temperature of 10 degree C. It was filled into tubs and stored at 5 degree C. A good and stable, high PUFA, low fat-continuous spread enriched with 10% stanol equivalents (mainly present as C18:0 stanol esters) was obtained.

Example 3b

Preparation of a Spread 40% (Opt. Ratio Ex.1b)

Refined sunflower oil was enriched with free and esterified stanols as obtained from Example 1b (to a total stanol equivalent concentration of 45%). Of this stanol and stanol-ester concentrate, 22 parts were mixed with 23 parts of normal refined sunflower oil and with 5 parts of a refined interesterified mixture of 50 parts fully hardened palm oil and 50 parts fully hardened palm kernel oil. To this fat blend small amounts of soybean lecithin, monoglyceride and beta-carotene solution were added.

To 44 parts water, gelatine and small amounts of whey protein powder, flavours, preservative and citric acid were added to obtain a pH of 4.7.

50parts of the fat phase composition (containing 40% of fat) and 48 parts of the aqueous phase composition were mixed and kept at 60 degree C. The mixture was then passed through a Votator line with 2 scraped surface heat exchangers (A-units) and 2 stirred crystallizers (C-unit), in ACAC-sequence operating at 500, 1000, 600 and 100 rpm respectively. The product leaving the last C-unit had a temperature of 10 degree C. It was filled into tubs and stored at 5 degree C. A good and stable, high PUFA, low fat-continuous spread enriched with 10% stanol equivalents (present as free and as C18:0 stanol esters) was obtained.

Example 4a

Preparation of a Dressing (Stanol Esters Ex.1a)

49 parts of water is mixed with 11 parts of various flavour components, preservatives, thickeners and emulsifiers. The mixture is thoroughly mixed in a stainless steel stirred vessel. To this aqueous mixture 20 parts of sunflower oil (65% PUFA as linoleic acid) enriched with 40% stanol equivalents present as stanol esters as obtained from Example 1a is added. To above oil in water mixture, 20 parts of normal refined sunflower oil is added, thoroughly mixed for an additional 15 min, to obtain a pre-emulsion. The pre-emulsion is brought into a colloid mill (Prestomill PM30) and processed at a split-size between level 15 and 20 and a throughput between level 4 and 6. A good and stable water continuous dressing enriched with 8% stanol equivalents (mainly present as C18:0 stanol esters) is obtained.

What is claimed is:

1. A process for the preparation of a mixture of stanol and stanol esters comprising esterification of phytosterols with a source of fatty acid moieties to a degree of esterification of the phytosterols in the range of 40–85%, and subsequently hardening the so obtained sterol/sterol fatty acid ester mixture.

2. Process according to claim 1, wherein the degree of esterification of the phytosterols is in the range of 55–80%.

3. The process according to claim 2 wherein the degree of esterification is in the range of 60–70%.

4. Process according to claim 1, wherein all steps of the process are carried out in such a manner that no solvents are needed.

5. Process according to claim 1, wherein the fatty acid groups of the stanol fatty acid esters are substantially saturated fatty acid esters.

6. Process according to claim 1, wherein the phytosterols are esterified with a source for fatty acid moieties comprising more than 70% of C18 polyunsaturated, monounsaturated and/or saturated fatty acid groups.

7. Food product comprising at least 1 wt % stanol equivalents present as a mixture of free stanols and fatty acid esterified stanols in a composition prepared according to the process of claim 1.

8. Food product according to claim 7, wherein at least 5 wt % of a mixture of 15–50% stanol and 50–85% stanol fatty acid esters is present.

9. Composition containing stanols wherein 15–60% stanols and 40–85% stanol fatty acid esters are present, and wherein the fatty acid groups of the stanol fatty acid esters are substantially saturated fatty acid groups.

10. Food product comprising at least 1 wt % stanol equivalents present as a mixture of free stanols and fatty acid esterified stanols in a composition according to claim 9.

11. Food product according to claim 10, wherein at least 3 wt %, and preferably at least 5 wt % stanol equivalents are present.

12. Food product according to claim 11, wherein the fat based food product is a yellow fat spread comprising 0–80% fat.

13. Food product according to claims 10, wherein the food product is a fat based food product.

14. Food product according to claim 13 wherein the fat used in the product is a fat comprising at least 30 wt %, of PUFA rich triglycerides, calculated on the total weight of the fat present in the product.

15. The food product according to claim 14 wherein the fat used comprises at least 45 wt. % of PUFA rich triglycerides.

* * * * *